(12) United States Patent
Genehr Alves

(10) Patent No.: US 11,944,829 B1
(45) Date of Patent: Apr. 2, 2024

(54) SELF-SEALING STRAIN RELIEF MECHANISM FOR IMPLANTABLE PULSE GENERATORS

(71) Applicant: BIOTRONIK SE & Co. KG, Berlin (DE)

(72) Inventor: Luis Genehr Alves, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 18/283,081

(22) PCT Filed: Mar. 17, 2022

(86) PCT No.: PCT/EP2022/056995
§ 371 (c)(1),
(2) Date: Sep. 20, 2023

(87) PCT Pub. No.: WO2022/200169
PCT Pub. Date: Sep. 29, 2022

Related U.S. Application Data

(60) Provisional application No. 63/165,256, filed on Mar. 24, 2021.

(51) Int. Cl.
*A61N 1/375* (2006.01)
*A61N 1/362* (2006.01)

(52) U.S. Cl.
CPC ............ *A61N 1/3752* (2013.01); *A61N 1/362* (2013.01)

(58) Field of Classification Search
None
See application file for complete search history.

(56) References Cited

U.S. PATENT DOCUMENTS

| | | | |
|---|---|---|---|
| 7,083,474 B1 | 8/2006 | Fleck et al. | |
| 2004/0267328 A1* | 12/2004 | Duffin | A61N 1/3752 607/37 |
| 2007/0100386 A1 | 5/2007 | Tronnes et al. | |
| 2013/0013042 A1 | 1/2013 | McDonald | |
| 2016/0015982 A1 | 1/2016 | Biele et al. | |
| 2020/0338335 A1 | 10/2020 | Deininger et al. | |

FOREIGN PATENT DOCUMENTS

WO    WO-0009204 A1 *  2/2000  ........... A61N 1/0565

OTHER PUBLICATIONS

International Search Report and Written Opinion for PCT/EP2022/056995 filed Mar. 17, 2022, 11 pages.

* cited by examiner

*Primary Examiner* — Kennedy Schaetzle
(74) *Attorney, Agent, or Firm* — FROST BROWN TODD LLP

(57) ABSTRACT

A medical implant is in the form of an implantable pulse generator. The implantable pulse generator includes a housing and a socket arranged on the housing for receiving an end portion of a lead. The socket provides a strain relief for the lead. The strain relief forms a sleeve which surrounds a through-opening for receiving the lead. A seal protrudes from an inner side of the sleeve facing the through-opening and is designed to sealably close the through-opening when no lead is inserted into the through-opening.

12 Claims, 2 Drawing Sheets

SELF-SEALING STRAIN RELIEF MECHANISM FOR IMPLANTABLE PULSE GENERATORS

Figure 1:
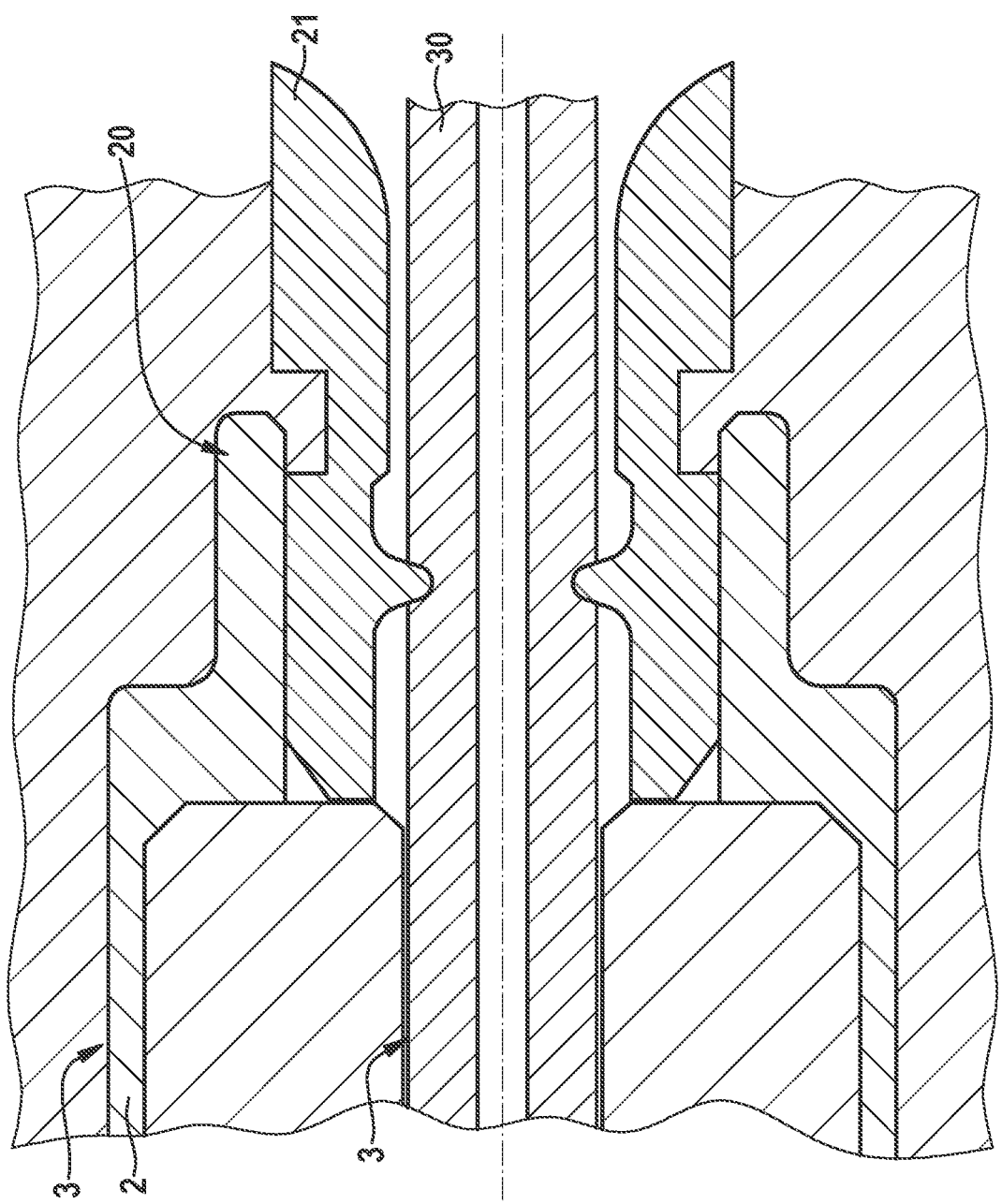

The present invention relates to a medical implant, particularly in the form of an implantable pulse generator (IPG).

A common use of an IPG without electrode leads connected thereto is to trial the size of a subcutaneous pocket in which to implant the IPG. Physicians routinely insert an IPG into the pocket prior to implantation to test the pocket size (this is referred to as trialing). Trialing requires the physician to seal the sockets of the IPG with plugs prior to trialing and then is remove the plugs before inserting the electrode leads into the sockets. This procedure is cumbersome because the plugs usually need to be secured with a set screw, and the plugs have handles that protrude from the IPG and can get caught in the tissue or break off. Alternatively, an IPG dummy can be used to check pocket size. Regardless of the solution used (dummy IPG or plugs), additional instruments are required to come into contact with the patient and the process is correspondingly time-consuming, leading physicians to skip this step.

Another common application is the use of an IPG where not all sockets need to be used for the prescribed therapy. The unused sockets are usually sealed with a plug to prevent fluid or debris from entering. In this scenario, the accumulation of fluid or debris may prevent the sockets from being used in the future, or leakage may occur between contacts within an exposed socket.

Based on this, the present invention is aimed at providing a medical implant that allows to reduce the number of instruments used in trialing that come into contact with the patient's body in order to reduce the risk of infection and to simplify the procedure. In particular, there should be no need to operate set screws to hold or release socket plugs. Further, in particular, the risk of breaking a plug shall be avoided, so as to ensure that no fragments remain in the IPG sockets, which could render the device unusable.

This problem is solved by a medical implant having the features of claim 1. Preferred embodiments of the invention are stated in the dependent claims and are described below.

According to claim 1, a medical implant is disclosed, in particular in the form of an implantable pulse generator (e.g., pacemaker), comprising:
 a housing, and
 a socket arranged on the housing for receiving an end portion (e.g. in the form of a plug) of a lead (e.g. electrode lead), the socket having a strain relief for the lead.

According to the invention, the strain relief forms a sleeve which surrounds a through-opening for receiving the lead, wherein a seal (e.g. a circumferential sealing lip) protrudes from an inner side of the sleeve facing the through-opening, which seal is designed to close the through-opening in a sealing manner when no lead is inserted into the through-opening, and which seal is designed to lie in a sealing manner against an end portion of the lead and thereby provide strain relief for the lead when the end portion is inserted into the through-opening as intended.

In this way, the invention provides a strain relief mechanism that seals the socket of the medical implant when not in use to prevent the ingress of fluids and debris. By using the strain relief to seal the socket, no plugs are needed to accomplish this purpose. Further, no tools are required to create the opening for the cable or an appropriate plug. The lead itself opens the seal to allow insertion.

Since the sockets according to the invention are already sealed without electrode lead, separate IPG dummies are no longer required for sizing/checking the subcutaneous pocket. After sizing verification, the implant can be used without the need to remove plugs from the respective socket or remove debris from inside the socket. When implanting, there is also the advantage that the respective socket is sealed, so that it is not necessary to use a plug to seal an unoccupied socket for implantation.

According to an embodiment of the present invention, the seal completely fills the through-opening for the end portion of the lead when the end portion is not inserted into the socket.

According to a further embodiment of the present invention, the seal is formed by a membrane. Particularly, in an embodiment of the invention, the membrane is pierced when the end portion of the lead is inserted into the through-opening. Furthermore, in an embodiment of the invention, the membrane is expanded when the end portion of the lead is inserted into the through-opening.

According to yet another embodiment of the present invention, the seal is a circumferential sealing lip.

Furthermore, according to an embodiment of the invention, the seal comprises thin sections to facilitate insertion of the lead through the seal or to control exactly how/where the seal, particularly membrane, tears to allow passage of the lead.

Further, according to an embodiment of the invention, the seal comprises pre-drilled holes to facilitate insertion of the lead through the seal or to control exactly how/where the seal, particularly membrane, tears to allow passage of the lead.

Furthermore, according to an embodiment of the invention, the seal comprises tearable sections to facilitate insertion of the lead through the seal or to control exactly how/where the seal, particularly membrane, tears to allow passage of the lead.

Further, according to yet another embodiment of the invention, the seal hermetically seals the socket to prevent ingress of foreign matter.

Figure 2:
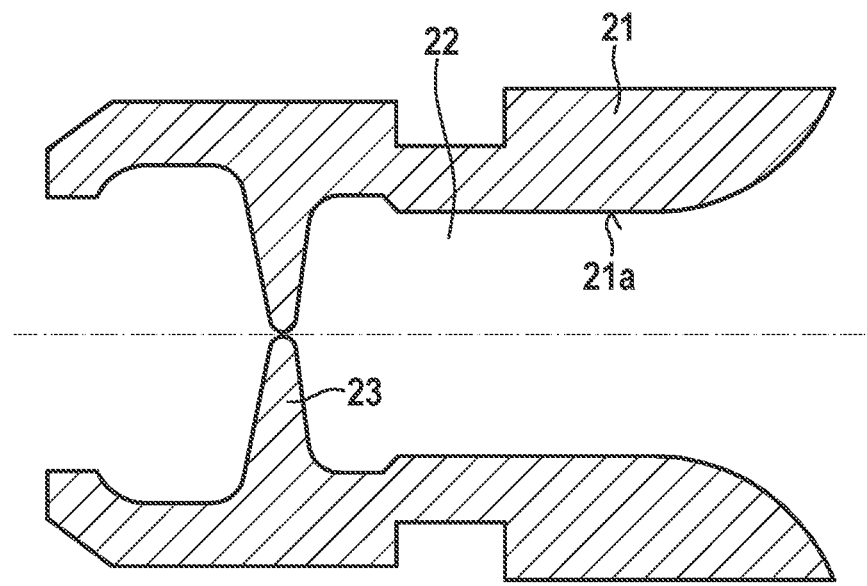
Figure 3:
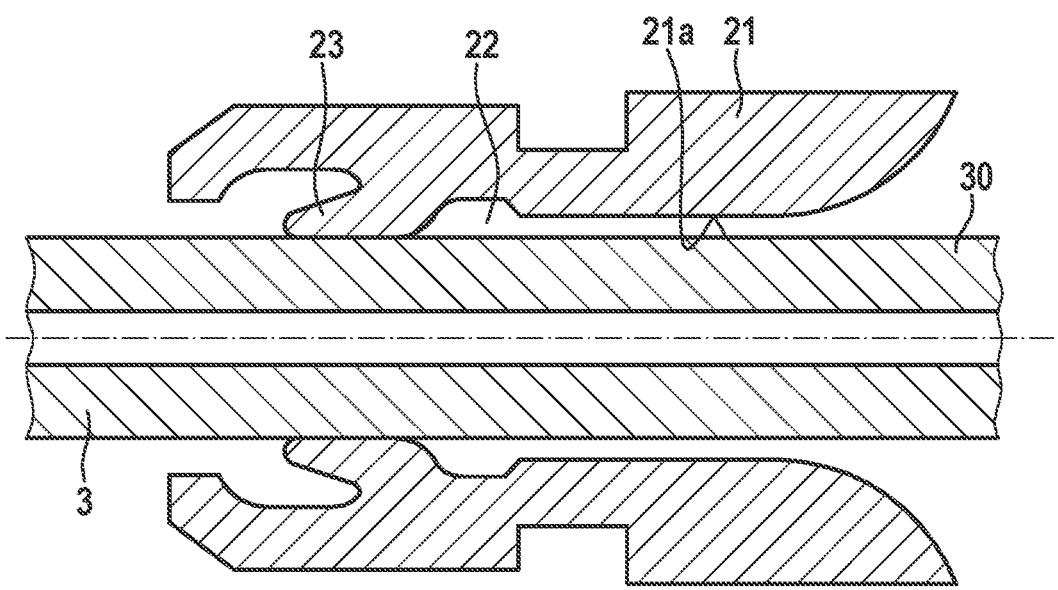

In the following, embodiments of the invention and further features and advantages of the invention will be explained with reference to the figures. Showing:

FIG. 1 schematic sectional view of a prior art strain relief for an electrode lead of an implantable pulse generator, FIG. 2 schematic sectional view of a strain relief of an embodiment of a medical implant according to the invention without an inserted electrode lead; and FIG. 3 schematic sectional view of the strain relief shown in FIG. 2 with the electrode lead inserted.

FIG. 1 shows a medical implant 1 with a housing 2 and a socket 20 for inserting an end portion 3 of an electrode lead 30. By modifying the design of the strain relief 21, which is constructed to create a seal when the end portion 3 is inserted into the socket 20, an implant 1 according to the invention as shown in FIGS. 2 and 3 can be realized. Here, it is provided that the strain relief 21 has a seal 23 that completely fills a through opening 22 for the end portion (e.g., plug) 3 or the electrode lead 30 when it is not inserted into the socket 20 (cf. FIG. 1). The seal 23 can be formed by a membrane which is pierced or expanded when the end portion 3 of the lead 30 is inserted into the opening 22.

The strain relief 21 is designed in particular as a sleeve 21 which surrounds the through-opening 22 for receiving the end portion 3 of the lead 30, the said seal 23 projecting from an inner side 21a of the sleeve 21 facing the through-opening 22, which seal 23 is designed, for example, as shown in FIG. 2, as a circumferential sealing lip 23 or alternatively as a pierceable membrane. The seal 23 is designed to seal the through-opening 22 when no lead is inserted into the through-opening 22 (see FIG. 2). The seal 23 is further designed to sealingly abut against an end portion 3 or the electrode lead 30 and thereby provide strain relief 21 for the lead 30 when it is inserted into the through opening 22 as intended (see FIG. 3).

Features such as thin sections, pre-drilled holes (such as shown in FIG. 2), or other easily tearable sections of the membrane/seal 23 can be used to facilitate insertion of the lead 30 through the membrane/seal 23 or to control exactly how/where the membrane 23 tears to allow passage of the lead 30. The diaphragm/seal 23 need not hermetically seal the port to prevent ingress of foreign matter, although a design could potentially be hermetically sealed if desired.

The solution according to the invention eliminates the need to seal unused sockets with separate plugs. Thus, there is no inconvenience for the patient or physician due to plugs protruding from the IPG body. The strain relief advantageously has a low profile.

The invention claimed is:

1. Medical implant (1) comprising:
   a housing (2), and
   a socket (20) arranged on the housing (2) for receiving an end portion (3) of a lead (30), the socket (20) having a strain relief (21) for the lead (30),
   characterized in that
   the strain relief forms a sleeve (21) which surrounds a through-opening (22) for receiving the end portion (3), wherein a seal (23) protrudes from an inner side (21a) of the sleeve (21) facing the through-opening (22), wherein the sleeve (23) is designed to sealably close the through-opening (22) when no end portion (3) of a lead (30) is inserted into the through-opening (22), and to sealingly abut against an end portion (3) of a lead (30) and thereby provide a strain relief for the lead (30) when the end portion (3) is inserted into the through-opening (22).

2. The medical implant according to claim 1, wherein the seal (23) completely fills the through opening (22) for the end portion when it is not inserted into the socket (20).

3. The medical implant according to claim 1, wherein the seal (23) is formed by a membrane.

4. The medical implant according to claim 3, wherein the membrane is pierced when the end portion (3) of the lead (30) is inserted into the through-opening (22).

5. The medical implant according to claim 3, wherein the membrane is expanded when the end portion (3) of the lead (30) is inserted into the through-opening (22).

6. The medical implant according to claim 1, wherein the seal is formed as a circumferential sealing lip (23).

7. The medical implant according to claim 1, wherein the seal (23) comprises thin sections to facilitate insertion of the lead (30) through the seal (23) or to control exactly how/where the seal (23) tears to allow passage of the lead (30).

8. The medical implant according to claim 1, wherein the seal (23) comprises pre-drilled holes to facilitate insertion of the lead (30) through the seal (23) or to control exactly how/where the seal (23) tears to allow passage of the lead (30).

9. The medical implant according to claim 1, wherein the seal (23) comprises tearable sections to facilitate insertion of the lead (30) through the seal (23) or to control exactly how/where the seal (23) tears to allow passage of the lead (30).

10. The medical implant according to claim 1, wherein the seal (23) hermetically seals the socket (20) to prevent ingress of foreign matter.

11. The medical implant according to claim 1, wherein the medical implant is an implantable pulse generator.

12. The medical implant according to claim 1, wherein the medical implant is a pacemaker.

* * * * *